(12) United States Patent  
Aysin et al.

(10) Patent No.: US 11,081,232 B2
(45) Date of Patent: Aug. 3, 2021

(54) MEDICAL DEVICE DATA MANAGEMENT CONFIGURATION SYSTEMS AND METHODS OF USE

(71) Applicant: Roche Diabetes Care, Inc., Indianapolis, IN (US)

(72) Inventors: Benhur Aysin, Fishers, IN (US); Siva Chittajallu, Indianapolis, IN (US); Michael Flis, East Carmel, IN (US); James Long, Noblesville, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 92 days.

(21) Appl. No.: 15/986,979

(22) Filed: May 23, 2018

(65) Prior Publication Data

US 2019/0362841 A1    Nov. 28, 2019

(51) Int. Cl.
*G06F 9/445* (2018.01)
*G16H 40/63* (2018.01)
(Continued)

(52) U.S. Cl.
CPC ............... *G16H 40/63* (2018.01); *G06F 8/65* (2013.01); *G06F 9/44505* (2013.01); *G06N 3/04* (2013.01);
(Continued)

(58) Field of Classification Search
CPC .......................... G16H 40/63; G06F 9/44505
See application file for complete search history.

(56) References Cited

U.S. PATENT DOCUMENTS 9,980,140 B1    5/2018 Spencer et al.
2009/0192813 A1    7/2009 Gejdos et al.
(Continued)

FOREIGN PATENT DOCUMENTS

CN    107982605 A    5/2018
EP    3042676 A1    7/2016
(Continued)

OTHER PUBLICATIONS

International Search Report and Written Opinion dated Sep. 3, 2019 relating to International Application No. PCT/US2019/033446.
(Continued)

*Primary Examiner* — Kim Huynh
*Assistant Examiner* — Eric Chang
(74) *Attorney, Agent, or Firm* — Dinsmore & Shohl, LLP (57) ABSTRACT

Medical device data manager configuration methods and systems including a medical device, a smart mobile device including a camera, a processor, a memory communicatively coupled to the processor, and machine readable instructions stored in the memory that may cause a system to perform at least the following when executed by the processor: use the camera of the smart mobile device to capture an image of the medical device; apply an identification algorithm to the image of the medical device; identify the medical device as an identified medical device based on the image of the medical device and the identification algorithm; and automatically configure a software application tool on the smart mobile device to retrieve data associated with one or more requirements of the identified medical device.

19 Claims, 5 Drawing Sheets

(51) Int. Cl.
G06F 8/65 (2018.01)
G06N 3/04 (2006.01)
G06N 3/08 (2006.01)
G06K 7/14 (2006.01)
G06K 9/46 (2006.01)
G06K 9/62 (2006.01)

(52) U.S. Cl.
CPC .............. *G06N 3/08* (2013.01); *G06K 7/1417* (2013.01); *G06K 9/46* (2013.01); *G06K 9/6217* (2013.01)

(56) References Cited

U.S. PATENT DOCUMENTS

| | | | |
|---|---|---|---|
| 2011/0290871 A1 | 12/2011 | Jon et al. | |
| 2014/0266639 A1* | 9/2014 | Zises | G08C 17/02 340/12.28 |
| 2014/0267770 A1* | 9/2014 | Gervautz | H04N 5/23296 348/169 |

FOREIGN PATENT DOCUMENTS

| | | |
|---|---|---|
| WO | WO2005045401 A1 | 5/2005 |
| WO | 2014165172 A1 | 10/2014 |
| WO | 2014174118 A1 | 10/2014 |
| WO | 2015059306 A1 | 4/2015 |
| WO | 2016092448 A1 | 6/2016 |
| WO | 2017125550 A1 | 7/2017 |

OTHER PUBLICATIONS

Naagaraj, "Implementing QR Code Technology in Medical Device Package", Jan. 1, 2009, pp. 1-98,https://scholarworks.rit.edu/theses/9349/; retrieved on Aug. 22, 2019.

Annoymous: "Guide on Unique Device Identification (UDI) Implementation In the USA and in the EU", Mar. 1, 2017, pp. 1-9; URL:https://www.gsl.org/sites/default/file s/docs/healthcare/position-papers/gsl udi guide final 20170324.pdf retrTeved on Aug. 22, 2019.

Annoymous, Implementing Unique Device Identification. Recommendations for Integrating Medical Device Data Throughout the Health Care System, Sep. 1, 2015, https://www.pewtrusts.org/-/media/assets/2015/09/udiimplementation-report.pdf; retrieved on Aug. 23, 2019.

* cited by examiner

MEDICAL DEVICE DATA MANAGEMENT CONFIGURATION SYSTEMS AND METHODS OF USE

TECHNICAL FIELD

The present specification generally relates to data manager configuration systems to configure a mobile device with respect to a medical device and, more specifically, to medical device data manager configuration systems to identify a medical device and configure a mobile smart device based on the identified medical device and methods of use of such systems.

BACKGROUND

A mobile device may include software to retrieve information about a medical device after user self-selection of the medical device from a list. Such software requires the selected medical device to be on the list as well as user input that may disjoint the process and lead to potential human error due to an incorrect selection of the medical device from the list.

Accordingly, a need exists for alternative systems to streamline medical device configuration on a mobile device with respect to a medical device and methods of use of such systems.

SUMMARY

In one embodiment, a medical device data manager configuration system may include a medical device, a smart mobile device including a camera, a processor, a memory communicatively coupled to the processor, and machine readable instructions stored in the memory. The machine readable instructions may cause the medical device data manager configuration system to perform at least the following when executed by the processor: use the camera of the smart mobile device to capture an image of the medical device; apply an identification algorithm to the image of the medical device; identify the medical device as an identified medical device based on the image of the medical device and the identification algorithm; and automatically configure a software application tool on the smart mobile device to retrieve data associated with one or more requirements of the identified medical device.

In one other embodiment, a method of operating a medical device data manager configuration system may include capturing an image of a medical device through a camera on a smart mobile device; applying an identification algorithm to the image of the medical device; identifying the medical device as an identified medical device based on the image of the medical device and the identification algorithm; and automatically configuring a software application tool on the smart mobile device to retrieve data associated with one or more requirements of the identified medical device as retrieved data. The software application tool may include a GUI on a display screen of the smart mobile device. The method may further include pairing the software application tool with the identified medical device based on the retrieved data such that the smart mobile device is communicatively coupled to the identified medical device; monitoring, as a monitored activity of the identified medical device by the software application tool, an administration of a prescribed treatment regime for the user through use of the identified medical device to administer the prescribed treatment regime; and providing an alert on the GUI and to the user of a failure in the administration of the prescribed treatment regime based on the monitored activity of the identified medical device by the software application tool.

In yet one other embodiment, a method of operating a medical device data manager configuration system may include capturing an image of a medical device through a camera on a smart mobile device; applying an identification algorithm to the image of the medical device; and identifying the medical device as an identified medical device based on the image of the medical device and the identification algorithm; presenting an option to the user to accept the identified medical device. The method may further include, in response to acceptance by the user of the option to accept of the identified medical device, automatically configuring a software application tool on the smart mobile device to retrieve data associated with one or more requirements of the identified medical device as retrieved data including at least setup content; pairing the software application tool with the identified medical device based on the setup content such that the smart mobile device is communicatively coupled to the identified medical device; and monitoring as a monitored activity the identified medical device by the software application tool of the smart mobile device.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Referring generally to the figures, embodiments of the present disclosure are directed to medical device data manager configuration systems to identify a medical device and configure a mobile smart device based on the identified medical device and methods of use of such systems. For example, multiple medical devices are available and provided for multiple worldwide markets. Data management solutions that communicate with these medical devices are utilized by users such as diabetic persons to more effectively manage their diabetic conditions. However, each medical device is unique in respect to its respective requirements to operate with such data management solutions, and each market may be distinct with respect to type of offered medical device and respective intended use and performance.

The medical device data manager configuration systems described herein streamline a process to select a medical device to more efficiently and accurately pair with the smart mobile device 102 by not requiring manual user selection, for example, of the medical device from a listing of options presented to the user. Further, by not being restricted to a listing of medical device selection options as viewable on a screen for user selection, a field of potentially identifiable medical devices able to be synched or paired with the system(s) is greatly increased. Additionally, the field of potentially identifiable medical devices may be restricted by country type and/or other restrictions, as described in greater detail further below. Additionally, removing user-based selection steps that would require additional processing steps reduces an amount of processing time along with reducing a potential of human error, thereby increasing and improving processing speed and accuracy of the systems described herein.

Moreover, pre-marketing risks associated with listing an unavailable device, risks of user confusion, and/or low confidence of proper device selection from a list by the user may be risks associated with manual user selection options. Rather, the systems described herein may employ a software application tool as a data manager that is communicatively coupled to a smart mobile device to capture an image of the medical device. The software application tool may be configured to automatically identify the medical device based on the captured image to retrieve data associated with the identified medical device. The system is able to use the retrieved data to pair the identified medical device with the smart mobile device and to monitor activity of the identified medical device through use of the smart mobile device.

Reference will now be made in detail to embodiments of the medical device data manager configuration systems, and examples of such systems are illustrated in the accompanying drawings. Wherever possible, the same reference numerals will be used throughout the drawings to refer to the same or like parts. Various embodiments of the medical device data manager configuration systems will be described in further detail herein with specific reference to the appended drawings.

Figure 1:
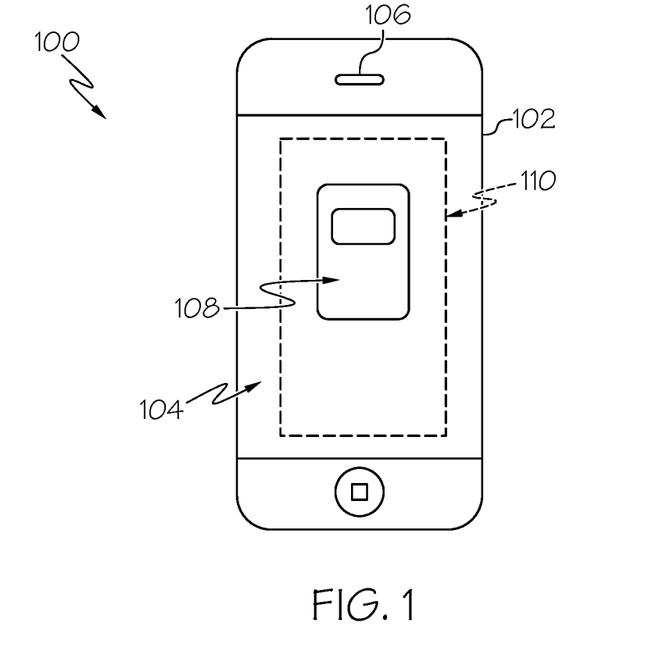
FIG. 1 schematically illustrates a medical device data manager configuration system during image capture of a medical device to identify the medical device, according to one or more embodiments shown and described herein.

Referring to FIG. 1, a medical device data manager configuration system 100 includes a smart mobile device 102 including a display screen 104 and a camera 106. The medical device data manager configuration system 100 further includes a medical device 108. The medical device may be a blood glucose meter, a continuous glucose monitor, an insulin pump, an insulin, a wellness device, or a like medical device. By way of example and not as a limitation, a wellness device may be a device configured to improve the wellness of an individual through tracking wellness data associated with the health and wellness of the individual and/or monitoring activity of the individual. Such wellness data may include, for example, vital signs including heart rate, calories consumed and burned, and cholesterol levels. The monitored activity of the individual may include a number of steps taken in a time period or another fitness activity conducted by the individual such as running, cycling, or hiking.

Further, the medical device data manager configuration system 100 includes a processor and a memory communicatively coupled to the processor, such as the processor 304 and memory component 306 as described with respect to FIG. 3 in greater detail further below. The medical device data manager configuration system 100 includes machine readable instructions stored in the memory that cause the medical device data manager configuration system 100 to perform one or more of instructions when executed by the processor.

The machine readable instructions may include instructions to use the camera 106 of the smart mobile device 102 to capture an image 111 of the medical device 108. A software application tool 112 (FIG. 2) on the smart mobile device 102 may be configured to display a reference frame 110 (FIG. 1) on the display screen 104 of the smart mobile device 102. The reference frame 110 may be configured to identify an area to position the medical device 108 within prior to image capture by the camera 106 of the smart mobile device 102. Use of such a reference frame 110 may allow for a more robust image capture by enabling a user to capture device images that are roughly similar in size, for example. In at least one embodiment, the software application tool 112 on the smart mobile device 102 may be communicatively coupled to the camera 106 such that an option to capture an image may be displayed for selection and one or more menu options for selection on the display screen 104. In response to selection of the capture an image option, the software application tool 112 provides logic instructions to turn on the camera 106 and place the reference frame 110 on the display screen 104 of the smart mobile device 102 at a predetermined location on the display screen 104. Location and/or size of the reference frame 110 on the display screen 104 may be fixed and pre-determined. In response to image capture, the reference frame 110 disappears from the display screen 104 and the image 111 is displayed on the display screen 104 with an option to accept or rejection the image for user selection. In response to user acceptance of the image 111, the image 111 is analyzed by an identification algorithm 312A to identify the medical device 108 in the image 111 as an identified medical device 108A.

The machine readable instructions may include further instructions to apply the identification algorithm 312A to the image 111 of the medical device 108. In embodiments, the image 111 is a picture or a video. The image 111 may be a frontal image of the medical device 108 or a rear image of the medical device 108. The image 111 is of the medical device 108 with a medical device display screen that is turned on with a back-lit background, for example, to include display information configured to be utilized as input for the identification algorithm 312A. In at least one embodiment, the identification algorithm 312A does not require the medical device 108 to be turned on when capturing the image 111 of the medical device 108, as the identification algorithm 312A may be trained, as described in greater detail further below, on images of medical devices that are not turned on. Should the display information of a medical device 108 that is turned on for image capture as the image 111 be captured, however, the display information may provide identifying characteristics for use with the identification algorithm 312A to determine the identified medical device 108. By way of example and not as a limitation, such identifying characteristics may include a particular display color and/or particular display text that the identification algorithm 312A may be retrained to include as input in addition to identifying characteristics already included in a trained convolutional neural network 313 used with the identification algorithm 312A, as illustrated in FIG. 3.

The machine readable instructions may include further instructions to identify the medical device as an identified medical device 108A based on the image 111 of the medical device 108 and the identification algorithm 312A. The identification algorithm 312A may be administered through an identification tool component 312, as described in greater detail below with respect to FIG. 3.

In embodiments, the identification algorithm 312A may further include at least one of reading of a QUICK RESPONSE CODE ("QR code"), a serial number, a Unique Device Identifier (UDI), or a Globally Unique Identifier (GUID) of the medical device 108. In at least one embodiment, a UDI may be found on the back of a medical device 108 and/or the medical device 108 may meet particular Global Harmonization Task Force (GHTF) requirements. By way of example and not as a limitation, the UDI is a unique numeric or alphanumeric code, required by the Food and Drug Administration in the United States of America, including a device identified specific to a device model of a medical device 108 and a production identifier. The production identifier includes current production information for the specific medical device 108 such as lot serial number, expiration date, and the like. The GUID may be a 128-bit number created by a system, such as a Microsoft Windows® operating system or other Microsoft Windows® application or like system, to uniquely identify specific components, hardware, software, files, user accounts, database entries, and other like items. The identification algorithm 312A may be an image recognition algorithm. The image recognition algorithm may be configured to utilize a neural network, and the neural network may be customizable. The image recognition algorithm may be configured to utilize a convolutional neural network that, in a field of machine learning, for example, is a class of deep, feed-forward artificial neural networks applied for image analysis. As a non-limiting example, the image recognition algorithm is generated from a program including ALEXNET, INCEPTION (GOOGLE-NET), BN-INCEPTION-V2, and/or INCEPTION-V3.

The image recognition algorithm may be configured to utilize the trained convolutional neural network 313. The trained convolutional neural network 313 may be configured to identify objects within an image to a high-level of accuracy. As an example and not a limitation, the trained convolutional neural network 313 is pre-trained on a subset of an image database, which may be a database 314 as described in greater detail below with respect to FIG. 3, for example. The trained convolutional neural network 313 may be trained on more than a million images and configured to classify images into at least a thousand categories. The trained convolutional neural network 313 may pre-trained on a subset of a medical device image database 315, which may be included as or within the database 314 as described in greater detail below, and comprises one or more coefficients configured to detect one or more types of medical devices 108. The trained convolutional neural network 313 may be trained to detect objects such that effect of orientation, light conditions, and image depth are minimal on accuracy of identification.

In at least one embodiment and as a non-limiting example, layers of an example trained convolutional neural network 313 are set forth below in TABLE 1:

TABLE 1

| Layer No. | Identifier Term | Term Definition | Description |
|---|---|---|---|
| 1 | 'data' | Image Input | 227 × 227 × 3 images with 'zerocenter' normalization |
| 2 | 'conv1' | Convolution | 96 11 × 11 × 3 convolutions with stride [4 4] and padding [0 0 0 0] |
| 3 | 'relu1' | ReLU | ReLU |
| 4 | 'norm1' | Cross Channel Normalization | Cross channel normalization with 5 channels per element |
| 5 | 'pool1' | Max Pooling | 3 × 3 max pooling with stride [2 2] and padding [0 0 0 0] |
| 6 | 'conv2' | Convolution | 256 5 × 5 × 48 convolutions with stride [1 1] and padding [2 2 2 2] |
| 7 | 'relu2' | ReLU | ReLU |
| 8 | 'norm2' | Cross Channel Normalization | Cross channel normalization with 5 channels per element |
| 9 | 'pool2' | Max Pooling | 3×3 max pooling with stride [2 2] and padding [0 0 0 0] |
| 10 | 'conv3' | Convolution | 384 3 × 3 × 256 convolutions with stride [1 1] and padding [1 1 1 1] |
| 11 | 'relu3' | ReLU | ReLU |
| 12 | 'conv4' | Convolution | 384 3 × 3 × 192 convolutions with stride [1 1] and padding [1 1 1 1] |
| 13 | 'relu4' | ReLU | ReLU |
| 14 | 'conv5' | Convolution | 256 3 × 3 × 192 convolutions with stride [1 1] and padding [1 1 1 1] |
| 15 | 'relu5' | ReLU | ReLU |
| 16 | 'pool5' | Max Pooling | 3 × 3 max pooling with stride [2 2] and padding [0 0 0 0] |
| 17 | 'fc6' | Fully Connected | 4096 fully connected layer |
| 18 | 'relu6' | ReLU | ReLU |
| 19 | 'drop6' | Dropout | 50% dropout |
| 20 | 'fc7' | Fully Connected | 4096 fully connected layer |
| 21 | 'relu7' | ReLU | ReLU |
| 22 | 'drop7' | Dropout | 50% dropout |

TABLE 1-continued

| Layer No. | Identifier Term | Term Definition | Description |
|---|---|---|---|
| 23 | 'special 2' | Fully Connected | 64 fully connected layer |
| 24 | 'relu' | ReLU | ReLU |
| 25 | 'fc8 2' | Fully Connected | 4 fully connected layer |
| 26 | 'softmax' | Softmax | softmax |
| 27 | 'classoutput' | Classification Output | Crossentropyex with 'Aviva' and 3 other classes |

Each layer in a neural network has corresponding coefficients. For example, with respect to the 25th layer in the example neural network of TABLE 1 above, partial coefficients related to this layer are set forth below in TABLE 2:

TABLE 2

PARTIAL COEFFICIENTS RELATED TO 25TH LAYER OF TABLE 1

−0.0905 −0.0122 −0.0421 0.1393 0.0999 0.0206 −0.0306 −0.0398 0.0018 −0.0129 0.0329 0.0170 . . .
−0.0472 −0.0300 0.0522 −0.0988 −0.0483 −0.0202 0.0493 −0.0189 0.0327 −0.0102 −0.0300 −0.0971 . . .
0.0877 0.0309 −0.0504 −0.0407 0.0218 0.0025 0.0160 0.0393 −0.0393 0.0303 −0.0425 0.0043 . . .
0.0376 0.0327 −0.0050 −0.0082 −0.0650 −0.0086 −0.0108 0.0208 −0.0261 −0.0258 0.0312 0.0511 . . .

Such coefficients are determined during training and are set post training of the trained convolutional neural network 313, as described in greater detail further below. The coefficients are derived using a large dataset that is representative of multiple types of medical devices. During the training to optimize the neural network model, coefficients self-adjust to provide for most accurate predictions. Once a model is determined and optimized, the coefficients do not change for future predictions. A determined model is then used with determined and fixed coefficients to predict a type of a medical device. New set coefficients are created only when there is a re-training of the model in the future with and using additional data for the re-training.

In at least another embodiment and as a non-limiting example, the trained convolutional neural network 313 as described herein is trained using ALEXNET and an IMAGENET database. In particular, ALEXNET is the pre-trained convolutional neural network that is trained on a subset of the IMAGENET database through a model that is trained on more than a million images to classify the images into a thousand categories. For use with the identification algorithm 312A with respect to medical device as described herein, ALEXNET's capabilities are leveraged to fine-tune the trained convolutional neural network 313 to be able to identify a type of medical device 108 as described herein. For example, certain layers of the ALEXNET neural network are retrained into a fine-tuned, trained convolutional neural network 313 using the medical device image database 315 that includes multiple types of medical devices, each of which may be identified as the identified medical device 108A. This trained convolutional neural network 313 includes a structure similar to the structure of the ALEXNET neural network yet further includes coefficients designed to detect the different types of medical devices.

Performance of this trained convolutional neural network 313 may be tested on a test data set that was not part of the training of the trained convolutional neural network 313 to confirm acceptable operation of the trained convolutional neural network 313. Such a trained convolutional neural network 313 as described herein may be utilized in block 504 described further below, for example, as the network on which the identification algorithm 312A is run on the image 111 of the medical device 108 to determine the identified medical device 108A.

In at least one embodiment, and as described in greater detail below with respect to a process 400 of FIG. 4, a process 500 of FIG. 5, and/or a process 600 of FIG. 6, which may be implemented by a processor 304 of FIG. 3, a method of operating a medical device data manager configuration system may include programming logic such as at least one of the process 400, the process 500, and the process 600

Figure 6:
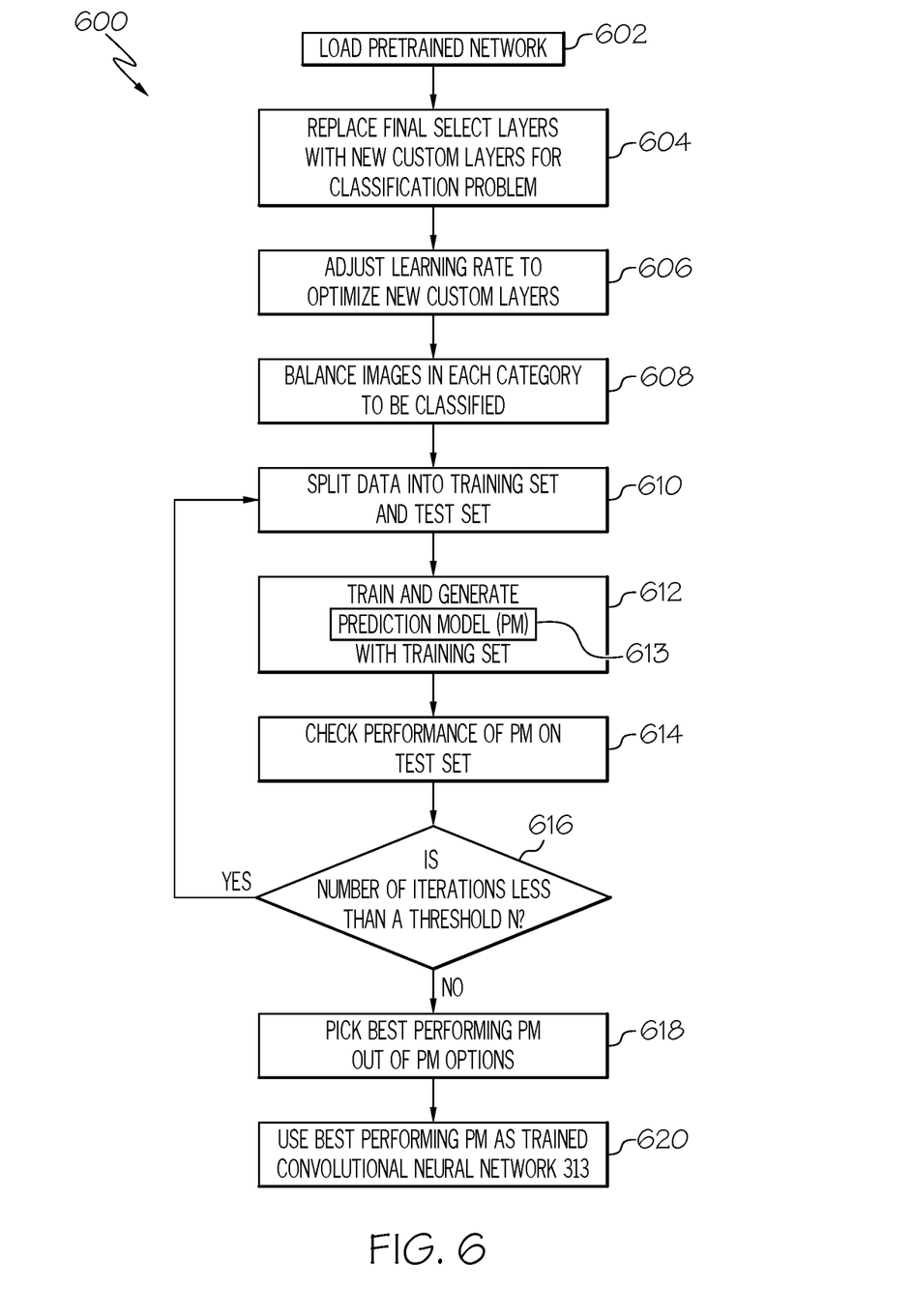
FIG. 6 is a flow chart of a process for configuring a neural network for use and operation with the medical device data manager configuration system of FIGS. 1 and 2, according to one or more embodiments shown and described herein.

As a non-limiting example, FIG. 6 illustrates a method or process 600 to train, retrain, and generate such a trained convolutional neural network 313. In block 602, a pre-trained convolutional neural network is loaded to a system. In at least one embodiment, the processor 304 is configured to execute one or more instructions to load the pre-trained convolutional neural network to the medical device data manager configuration system 100. In block 604, one or more select layers, such as final select layers, are replaced with new custom layers particular to the image and device classification problem described herein and through one or more instructions executed by the processor 304. As a non-limiting example, an ALEXNET neural network is loaded to the system through one or more instructions executed by the processor 304, the final three layers are removed through one or more instructions executed by the processor 304, and three new custom layers are added to replace the removed final three layers through one or more instructions executed by the processor 304.

In block 606, a learning rate is adjusted to optimize the new custom layers. In at least one embodiment, the processor 304 is configured to execute one or more instructions to adjust the learning rate to optimize the new custom layers. During optimization of a neural network, a learning rate may determine how slow or fast a training is progressing. However, such a learning rate is not arbitrarily chosen for optimization. Further, if a learning rate is too small, the training will progress slowly and network coefficients will change slowly, while if the rate is too high, the training may not be able to converge for model completion. As most of the ALEXNET network is pre-trained, and only a few new layers are added to the network to replace select previous layers, the learning rate is able to be adjusted in a way that the new added layers of block 604 are optimized while the coefficients for the pre-trained layers do not substantially change during training.

In block 608, images are balanced across each category to be classified. As set forth, the trained convolutional neural network 313 is pre-trained on an image database subset such as the medical device image database 315 of FIG. 3 and may be trained on more than a million images and be configured to classify the images into at least a thousand categories. In at least one embodiment, the processor 304 is configured to execute one or more instructions to balance the images across each such category to be classified.

In block 610, the network data set, which is the entire data set from the pre-trained network now modified to include new custom layers generated through blocks 602-608, may be split into a training set and a test set. In at least one embodiment, the processor 304 is configured to execute one or more instructions to split the network data set into the training set and the test set. As a non-limiting example, 70% of the network data set may be utilized as the training set and 30% of the network data set may be utilized as the test set. In block 612, the convolution neural network is trained and a prediction model 613 is generated with the training set. In at least one embodiment, the processor 304 is configured to execute one or more instructions to train the convolutional neural network and generate the prediction model 613 with the training set. In block 612, performance of the prediction model 613 is checked on the test set to determine confidence and accuracy levels of the prediction model 613 through, for example, one or more instructions executed by the processor 304.

For each neural network model, a limit is set for a number of optimization steps as a number of epochs to determine a minima for a best solution. During optimization, each model searches for the minima and repeats the search until the limit is reached for the number of epochs or until the model converges. At the end of this minima search based iterative process, only one prediction model 613 is generated.

During the training, the system further goes through a model determination based iterative process to determine multiple prediction models 613. In block 616, the process 600 determines whether the number of iterations I completed to determine each prediction model 613 is less than a threshold number N set for the model determination based iterative process through, for example, one or more instructions executed by the processor 304. The threshold value N may be a predetermined number, for example. If not, the process 600 returns to block 610 to repeat the minima search based iterative process to determine another prediction model 613 through blocks 612-614. If so, the process 600 advances to block 618 to select a best performing prediction model 613 out of the N options of determined prediction models 613. In block 620, the selected best performing prediction model 613 is used as the trained convolutional neural network 313. By repeating the model determination based iterative process N times, the process 600 may take advantage of different random sampling of the training set data and initial starting points. Based off different starting points and a unique distribution of the training set data, the process 600 may result in slightly different prediction models 613 with slightly different accuracies after each iteration of the model determination based iterative process. By repeating the model determination based iterative process N times through, for example, one or more instructions executed by the processor 304, the process 600 may determine N prediction models 613 with slightly differences in accuracy and select the prediction model 613 that presents the best performance as the final model to utilize as the trained convolution neural network 313 as described herein.

Figure 3:
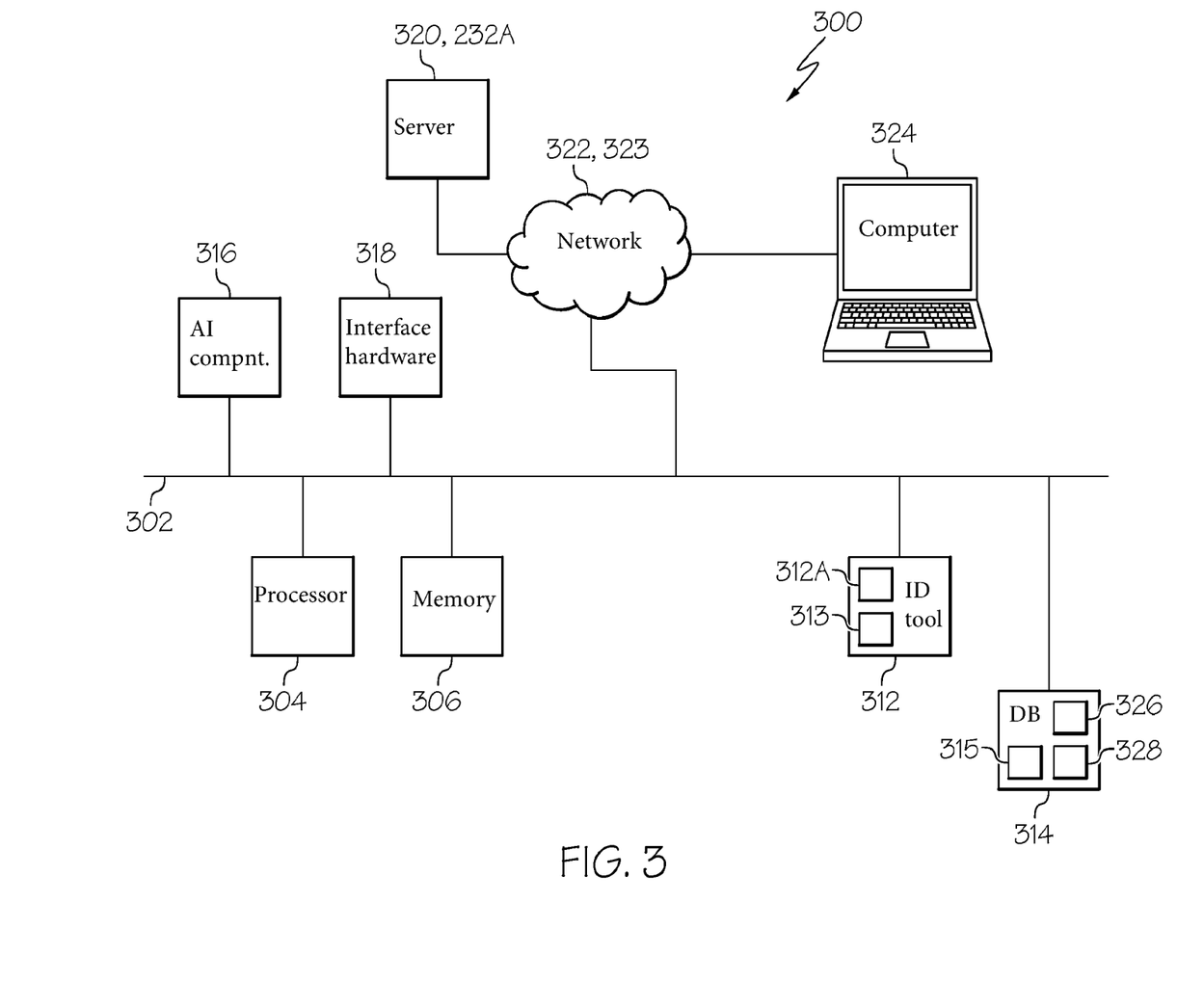

In embodiments, the trained convolutional neural network 313 and associated computations may be stored in the smart mobile device 102, and the image database 314 (e.g., the database 314 of FIG. 3), may be stored in a cloud networking environment (for example, referable to as "the cloud 323" as shown in FIG. 3, described in greater detail further below). Further, periodic retraining of the convolutional neural network may be performed in the cloud 323. An incorrect classification may be configured to trigger a retraining of the trained convolutional neural network 313. For example, a determination that of the incorrect classification would result in automatically sending a signal to the trained convolutional neural network 313 to request a retraining based on the incorrect classification. The training may occur automatically or at a scheduled time. The trained convolutional neural network 313 may be configured to be continuously retrained in response to a misclassification of a type of the medical device. As a non-limiting example, a misclassified image is added to a model training database with a correct label and the trained model convolutional neural network 313 is retrained to correctly classify the misclassified image. Further, the trained convolutional neural network 313 may be configured to have one or more updates made periodically as one or more updates are made to an associated convolutional network. For example, the one or more updates may be made at pre-scheduled times. In at least one embodiment, correctly identified images may be used to fine tune the trained convolutional neural network 313. As a non-limiting example, if the network is identifying images correctly but with a low-range identification confidence value, such as in a range of from about 60% to about 70%, for example, the one or more correctly identified images may be included in the image database 314 along with a 'correct' label. The 'correct' label may be applied to an image after a user manually confirms a predicted device type as predicted by the trained convolutional neural network 313. The 'correct' label may be further confirmed, prior to being used to retrain the trained convolutional neural network 313, after establishing a communication link between the data management application of the software application tool 112 and the medical device 108 such as through a Bluetooth pairing process. During such a pairing process, a device specific identifier 326 as shown in FIG. 3 may be passed to the data management application, and this device specific identifier 326 may be used to confirm the device type of the identified medical device 108A. For example, the device specific identifier 326 may be associated with a device list 328 stored in a database 314 that is accessible by the data management application of the software application tool 112. Increasing a number of representations of an image type of images capturing the medical device 108 in a large medical device image database 315 may assist with correct classification of such images with higher associated confidence values.

In embodiments, the smart mobile device 102 is configured to serve as a conduit to transfer the image 111 to a cloud server 323A of the cloud 323 (FIG. 3), and the cloud server 323A is configured to store the image database 314 and the trained convolutional neural network 313. For example, the image 111 is wirelessly transmitted to the cloud server 323A for prediction by the trained convolutional neural network 313 based on coefficients derived using a multitude of images stored in the image database. The trained convolutional neural network 313 is configured to interact with the identification algorithm 312A to predict and identify the medical device 108 as the identified medical device 108A as a device identification prediction based on the image 111 and the coefficients of the trained convolutional neural network 313. Information regarding the device identification prediction of the identified medical device 108A may then be wirelessly transmitted back to the smart mobile device 102 to be displayed to a user, for example. One or more identification calculations associated with the identification algorithm 312A are conducted in the cloud 323, and class information associated with the identified medical device 108A is transmitted to the smart mobile device 102 from the cloud 323. In at least one embodiment, when a new image 111 of a medical device 108 is received, the image 111 is input into the prediction model 613 of the trained convolutional neural network 313. The prediction model 613 determines a prediction of the type of the medical device as the identified medical device 108A. Images 111 may be stored in the image database for later use in training a new prediction model 613 to enhance future performance of a current prediction model 613.

The identification algorithm 312A may be configured to use one or more prediction confidence probabilities indicative of a confidence level associated with identification of the identified medical device 108A. A confidence threshold value may be associated with a positive identification of the identified medical device 108A such that the positive identification occurs in response to a prediction confidence probability this is greater than or equal to the confidence threshold value. The machine readable instructions may further comprise instructions to display a name of the identified medical device 108A on a graphical user interface (GUI) 114 of the display screen 104 of the smart mobile device 102 in response to the prediction confidence probability being greater than or equal to the confidence threshold value. The machine readable instructions further may include instructions to display an option for a user to accept or reject the name of the identified medical device 108A. Further, the machine readable instructions may include instructions to display a factory image of the identified medical device 108A alongside the image 111 of the medical device 108 in response to the prediction confidence probability being greater than or equal to the confidence threshold value. The machine readable instructions further may include instructions to display an option for a user to accept or reject the positive identification of the identified medical device 108A.

The smart mobile device 102 through, for example, the software application tool 112, may be configured to request a user to capture another image for analysis and identification in response to the prediction confidence probability being lower than the confidence threshold value. As a non-limiting example, the smart mobile device 102 is configured to request a user to capture another image of the medical device 108 in at least one of a different orientation or different environment in response to the prediction confidence probability being lower than the confidence threshold value.

Further, the machine readable instructions may include instructions to automatically configure the software application tool 112 on the smart mobile device to retrieve data associated with one or more requirements 116 of the identified medical device 108A. In at least one embodiment, once the device identification prediction is made to identify the identified medical device 108A, the software application tool 112 is configured to retrieve device specific data from the cloud 323. The cloud 323 may host multiple device specific data, and the software application tool 112 may identify and retrieve the device specific data associated with the identified medical device 108A from the multiple device specific data that is stored in the cloud 323. Such cloud storage may centralize the storage of the multiple device specific data to provide easy access and an ability to control and/or change such data and/or types selected for storage. Additionally or alternatively, such multiple device specific data for access by the software application tool 112 may be locally stored such that a remote transmission connection such as an internet connection is not required to access the device specific data. The machine readable instructions further may include instructions to display the one or more requirements 116 of the identified medical device 108A on the GUI 114 of the smart mobile device 102 to, for example and as described in greater detail below, inform the user of one or more requirements of the identified medical device. The GUI 114 is disposed on and as part of the display screen 104 of the smart mobile device 102 and is communicatively coupled to and controlled by the software application tool 112.

In embodiments, the one or more requirements 116 of the identified medical device 108A comprise content specific to the specific to the identified medical device 108A. Such content may include at least one of onboarding content, communication management instructions, educational materials, regulatory labeling content, and one or more menu options. For example, onboard content includes content associated with user training with respect to use of the identified medical device 108A for the first thirty days of use of the identified medical device 108A. The user training may include, for example, training on how to administer a therapeutic delivery agent with the identified medical device 108A according to a prescribed treatment regime for the user by a healthcare provider or the like.

The education materials may include educational content associated with the identified medical device 108A providing during a setup associated with the identified medical device 108A. As a non-limiting example, the educational content may include information about a compatible test strip, information about use of the compatible test strip with the identified medical device, and/or information about related calibration testing procedures. In embodiments, the setup associated with the identified medical device 108A may include configuration of the software application tool 112 to present instructions through a start-up wizard or first time user flow process of the software application tool 112 that is presented to the user to guide the user through setup of the identified medical device 108A. In at least one embodiment, the identified medical device 108A may be an identified blood glucose (BG) meter, and the start-up wizard for the identified blood glucose meter may include static and audio and/or video based instructional content as descriptions for instructions regarding, for example, setting BG test reminders, warning/alert thresholds, specific steps for wireless communication pairing, on-device feature configuration such as configuration of BG target range settings, and acquiring a blood sample. In at least one other embodiment, the identified medical device 108A may be an identified continuous blood glucose (BG) meter, and the start-up wizard for the identified continuous blood glucose meter may include static and audio and/or video based instructional content as descriptions for instruction regarding, for example, setting calibration test reminders, setting warning/alert thresholds, sounds used for specific audible alarms, specific steps for wireless communication pairing, sensor insertion, and on-device feature configuration such as configuration of continuous glucose target range settings.

The smart mobile device 102 may configured to be communicatively coupled to the identified medical device 108A. As an example and not a limitation, the machine readable instructions may include instructions to pair the smart mobile device 102 and the identified medical device 108A. The machine readable instructions may further include instructions to automatically provide device specific pairing instructional information to a user regarding pairing prior to pairing the smart mobile device 102 and the identified medical device 108A. By way of example and not as a limitation, a given identified medical device 108A may provide a PIN code on the display screen 104 during pairing when triggered to provide the PIN code through a user selection, such as through the user pressing an appropriate front-panel button on the identified medical device 108A. Devices without front-panel buttons may alternative include a printed fixed PIN code, such as a fixed PIN code printed upon a back of the identified medical device 108A. A user may be instructed where to find the printed fixed PIN code for pairing based on visual characteristics of the meter image, such as the identified medical device 108A including or not including such front-panel buttons. An additional security such as out of band pairing may be used to pair the smart mobile device 102 and the identified medical device 108A. Instruction may be provided for non-wireless communication methods for transferring data from the identified medical device 108A to a data repository, such as through instructions outlining required systems and steps to transfer data from the identified medical device 108A to a data repository through a protocol that is implement for a Universal Serial Bus (USB) device.

The machine readable instructions may further include instructions to automatically perform firmware version checks associated with the identified medical device 108A and/or install firmware updates associated with the identified medical device 108A. Upon identification of and subsequent connection to an identified medical device 108A, various device management tasks may be directed through use of the software application tool 112 and the identified medical device 108A. Such tasks may include downloading a firmware/software update for the identified medical device 108A for installation by a host system. Updates to associated systems in the field may occur after launch of the systems. The recognition of the identified medical device 108A could accordingly trigger a desired handling and update to the identified medical device 108A by an associated host system. Additionally, communication of device specific messaging from a manufacturer to an end user may occur any time after launch of the identified medical device 108A. By updating system responses in the cloud 323, timely messaging would thus be able to be enabled after recognition and launch of the identified medical device 108A. Further, as the identified medical device 108A may be configured to support one or more complex data analysis algorithms including at least a pattern recognition algorithm of one or more collected measurements, the smart mobile device 102 through the software application tool 112 may be configured to support one or more graphical tools configured to display one or more patterns based on the pattern recognition algorithm to a user. A particular medical device 108 may support more metadata, such as flags or annotations, than other medical devices 108. As such, recognizing a specific identified medical device 108A may allow the medical device data manager configuration system 100 to configure itself to support the metadata properly in terms of storage and visualization. The one or more patterns may be displayed to the user on the GUI 114 of the display screen 104 of the smart mobile device 102.

In embodiments, the identified medical device 108A is associated with one or more device specific labeling requirements. The instructions to automatically configure the software application tool 112 on the smart mobile device 102 to retrieve data associated with one or more requirements 116 of the identified medical device 108 may include instructions to retrieve and use the one or more device specific labeling requirements for the identified medical device 108A. For example, instructions to retrieve and use the one or more device specific labeling requirements for the identified medical device 108A from a database in which the labeling requirements are stored may further include instructions to display a unit of measure required for the identified medical device when displaying one or more measurement results on the GUI 114 of the display screen 104 of the smart mobile device 102. Additionally or alternatively, instructions to retrieve and use the one or more device specific labeling requirements for the identified medical device 108A may include instructions to display a warning, precaution, and/or limitation statement specific to and required by a health authority for the identified medical device 108A, such as a prescription device distribution control symbol (Rx). The one or more device specific labeling requirements to the identified medical device 108A may vary by country. For example, each country may have a specific, separately lead health authority setting country-specific regulations with respect to use of the identified medical device 108A, such as with respect to blood glucose unit of measure (e.g., mg/dL or mmol/L), local distributor contact information, operating condition limits (e.g., temperature and humidity), or direction regarding electronic labeling. Country or configuration specific information may further be useful to target removal and corrected activities with respect to identified adulterated devices in place of extending a recall activity for all distributed devices sharing a product name. The medical device data manager configuration system 100 may be configured to identify a country and retrieve country information related to the identified country through a signal generated by a global positioning system (GPS) sensor. Additionally or alternatively, the medical device data manager configuration system 100 may be configured to identify the country and retrieve country information related to the identified country through an image recognition algorithm as described herein that is further configured to recognize country specific information from the image 111 and/or another captured image.

Figure 2:
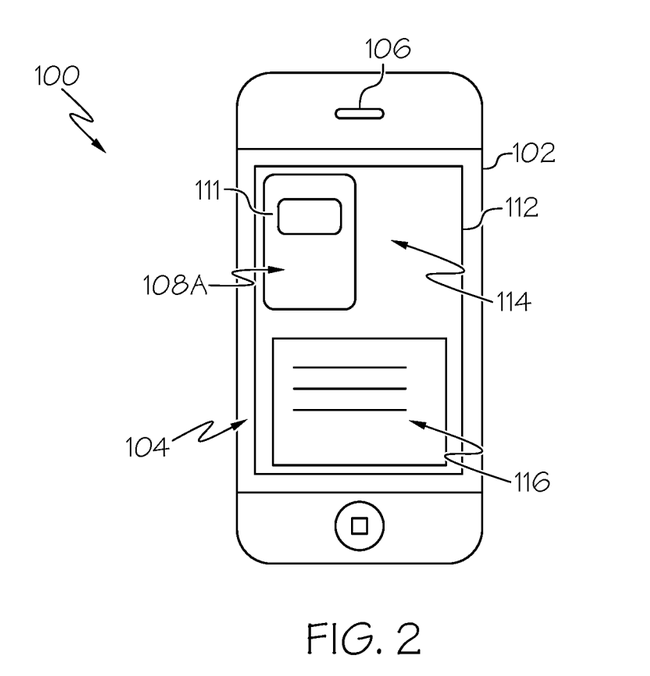
FIG. 2 schematically illustrates a medical device data manager configuration system after identification of the medical device and configuration of a mobile smart device based on the identified medical device, according to one or more embodiments shown and described herein FIG. 3 schematically illustrates a system for implementing computer and software based methods to utilize the medical device data manager configuration system of FIGS. 1 and 2, according to one or more embodiments shown and described herein.

Referring to FIG. 3, a system 300 for implementing a computer and software-based method to utilize the medical device data manager configuration system, as shown in FIGS. 1 and 2, is illustrated and may be implemented along with using a graphical user interface (GUI) that is accessible at a user workstation (e.g., a computer 324), for example. The system 300 includes a communication path 302, one or more processors 304, a memory component 306, an identification tool component 312, a storage or database 314 that may include the medical device image database 315, an artificial intelligence component 316, a network interface hardware 318, a server 320, a network 322, and at least one computer 324. The various components of the system 300 and the interaction thereof will be described in detail below.

While only one application server 320 and one user workstation computer 324 is illustrated, the system 300 can include multiple workstations and application servers containing one or more applications that can be located at geographically diverse locations across a plurality of industrial sites. In some embodiments, the system 300 is implemented using a wide area network (WAN) or network 322, such as an intranet or the Internet, or other wired or wireless communication network that may include a cloud computing-based network configuration (for example, the cloud 323 including the cloud server 323A). The workstation computer 324 may include digital systems and other devices permitting connection to and navigation of the network. Other system 300 variations allowing for communication between various geographically diverse components are possible.

The lines depicted in FIG. 3 indicate communication rather than physical connections between the various components.

As noted above, the system 300 includes the communication path 302. The communication path 302 may be formed from any medium that is capable of transmitting a signal such as, for example, conductive wires, conductive traces, optical waveguides, or the like, or from a combination of mediums capable of transmitting signals. The communication path 302 communicatively couples the various components of the system 300. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 300 includes the processor 304. The processor 304 can be any device capable of executing machine readable instructions. Accordingly, the processor 304 may be a controller, an integrated circuit, a microchip, a computer, or any other computing device. The processor 304 is communicatively coupled to the other components of the system 300 by the communication path 302. Accordingly, the communication path 302 may communicatively couple any number of processors with one another, and allow the modules coupled to the communication path 302 to operate in a distributed computing environment. Specifically, each of the modules can operate as a node that may send and/or receive data. The processor 304 may process the input signals received from the system modules and/or extract information from such signals.

As noted above, the system 300 includes the memory component 306 which is coupled to the communication path 302 and communicatively coupled to the processor 304. The memory component 306 may be a non-transitory computer readable medium or non-transitory computer readable memory and may be configured as a nonvolatile computer readable medium. The memory component 306 may comprise RAM, ROM, flash memories, hard drives, or any device capable of storing machine readable instructions such that the machine readable instructions can be accessed and executed by the processor 304. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 300 may include the processor 304 communicatively coupled to the memory component 306 that stores instructions that, when executed by the processor 304, cause the processor to perform one or more functions as described herein.

Still referring to FIG. 3, as noted above, the system 300 comprises the display such as a GUI on a screen of the computer 324 for providing visual output such as, for example, information, graphical reports, messages, or a combination thereof. The computer 324 may include one or more computing devices across platforms, or may be communicatively coupled to devices across platforms, such as mobile smart devices including smartphones, tablets, laptops, and/or the like or medical devices such as blood glucose meters, insulin pumps, continuous glucose monitors, and the like. The display on the screen of the computer 324 is coupled to the communication path 302 and communicatively coupled to the processor 304. Accordingly, the communication path 302 communicatively couples the display to other modules of the system 300. The display can include any medium capable of transmitting an optical output such as, for example, a cathode ray tube, light emitting diodes, a liquid crystal display, a plasma display, or the like. Additionally, it is noted that the display or the computer 324 can include at least one of the processor 304 and the memory component 306. While the system 300 is illustrated as a single, integrated system in FIG. 3, in other embodiments, the systems can be independent systems.

The system 200 comprises the identification tool component 312 to identify a medical device 108 as an identified medical device 108A through application of an identification algorithm 312A as described herein and an artificial intelligence component 316 to train and provide machine learning capabilities to a neural network associated with the identification algorithm 312A as described herein. The identification tool component 312 and an artificial intelligence component 316 are coupled to the communication path 302 and communicatively coupled to the processor 304. As will be described in further detail below, the processor 304 may process the input signals received from the system modules and/or extract information from such signals.

Data stored and manipulated in the system 300 as described herein is utilized by the artificial intelligence component 316, which is able to leverage a cloud computing-based network configuration such as the cloud 323 to apply Machine Learning and Artificial Intelligence. This machine learning application may create models that can be applied by the system 300, to make it more efficient and intelligent in execution. As an example and not a limitation, the artificial intelligence component 316 may include components selected from the group consisting of an artificial intelligence engine, Bayesian inference engine, and a decision-making engine, and may have an adaptive learning engine further comprising a deep neural network learning engine.

The system 300 includes the network interface hardware 318 for communicatively coupling the system 300 with a computer network such as network 322. The network interface hardware 318 is coupled to the communication path 302 such that the communication path 302 communicatively couples the network interface hardware 218 to other modules of the system 300. The network interface hardware 318 can be any device capable of transmitting and/or receiving data via a wireless network. Accordingly, the network interface hardware 318 can include a communication transceiver for sending and/or receiving data according to any wireless communication standard. For example, the network interface hardware 318 can include a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 3, data from various applications running on computer 324 can be provided from the computer 324 to the system 300 via the network interface hardware 318. The computer 324 can be any device having hardware (e.g., chipsets, processors, memory, etc.) for communicatively coupling with the network interface hardware 318 and a network 322. Specifically, the computer 324 can include an input device having an antenna for communicating over one or more of the wireless computer networks described above.

The network 322 can include any wired and/or wireless network such as, for example, wide area networks, metropolitan area networks, the Internet, an Intranet, the cloud 323, satellite networks, or the like. Accordingly, the network 322 can be utilized as a wireless access point by the computer 324 to access one or more servers (e.g., a server 320). The server 320 and any additional servers such as the cloud server 323A generally include processors, memory, and chipset for delivering resources via the network 322. Resources can include providing, for example, processing, storage, software, and information from the server 320 to the system 300 via the network 322. Additionally, it is noted that the server 320 and any additional servers can share resources with one another over the network 322 such as, for example, via the wired portion of the network, the wireless portion of the network, or combinations thereof.

Figure 4:
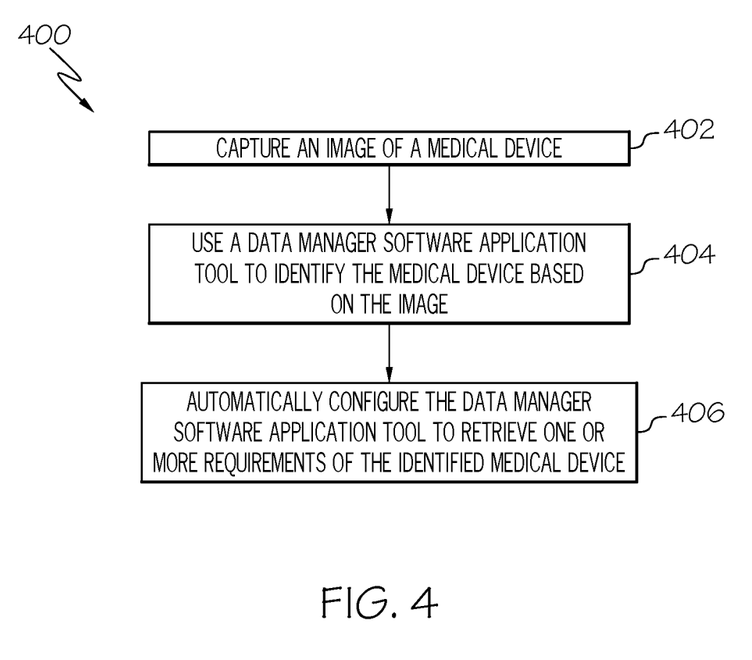
FIG. 4 is a flow chart of a process for using the medical device data manager configuration system of FIGS. 1 and 2, according to one or more embodiments shown and described herein.

FIG. 4 illustrates a method of operating or process 400 for operating the medical device data manager configuration system 100. In at least one embodiment, the processor 304 is configured to execute one or more instructions to implement the process 400. In block 402, an image 111 of a medical device 108 is captured. For example, the image 111 may be captured by a camera 106 of a smart mobile device 102 as described herein and through one or more instructions executed by the processor 304. In block 404, a data manager software application tool 112 of the smart mobile device 102 is used to identify the medical device 108 as an identified medical device 108A based on the image 111 as described herein. For example, an identification algorithm 312A is applied as described herein to the image 111 of the medical device 108 through one or more instructions executed by the processor 304 to identify the medical device 108 as an identified medical device 108A based on the image 111 of the medical device 108 and the identification algorithm 312A. In block 406, the data manager software application tool 112 on the smart mobile device 102 is configured to retrieve data associated with one or more requirements of the identified medical device 108A. In at least one embodiment, the processor 304 is configured to execute one or more instructions to retrieve data associate with the one or more requirements of the identified medical device 108A.

Figure 5:
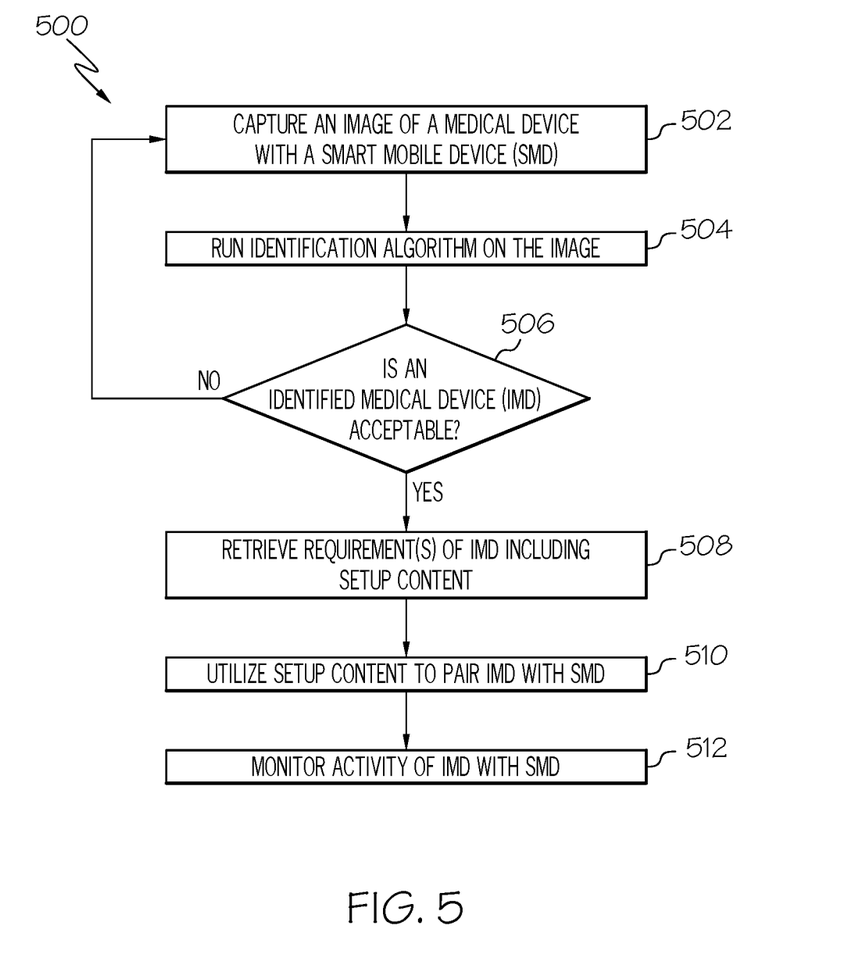
FIG. 5 is a flow chart of another process for using and operating the medical device data manager configuration system of FIGS. 1 and 2, according to one or more embodiments shown and described herein.

FIG. 5 illustrates another process 500 for operating the medical device data manager configuration system 100. In at least one embodiment, the processor 304 is configured to execute one or more instructions to implement the process 500. In block 502, an image 111 of the medical device 108 is captured with a camera 106 of the smart mobile device 102 as described herein and through, for example, one or more instructions executed by the processor 304 to capture the image 111 with the camera 106. In block 504, an identification algorithm 312A as described herein is run on the image 111 through application of the identification algorithm 312A by the identification tool component 312, for example, to the image 111 of the medical device 108. The medical device 108 is identified as an identified medical device 108A based on the image 111 of the medical device 108 and the identification algorithm 312A as described herein. In at least one embodiment, the processor 304 is configured to execute one or more instructions to run the identification algorithm 312A on the image 111 and identify the identified medical device 108A. In at least another embodiment, the identification algorithm 312A identified the identified medical device 108A based on the image 111 through use of the trained convolutional neural network 313 as described herein and above, such as the trained convolutional neural network that is fine-tuned and retrained for customizable use from an ALEXNET neural network trained on an IMAGENET database and further trained on the medical device image database 315 that includes multiple types of medical devices. Using the trained convolutional neural network, the medical device 108 in the image 111 is identified as the identified medical device 108A based on the applied coefficients and prediction model 613 of the trained convolutional neural network 313. In at least one embodiment, the identified medical device 108A is determined by the trained prediction model 613 based on one or more device features. Such features are created within the trained convolutional neural network 313 using convolution of the image 111 and pre-determined filters applied in early layers of the trained convolutional neural network 313 as described above. Once a prediction model 613 is fine-tuned and retrained as described above, this prediction model 613 may be used to identify the medical device 108 of the image 111 to predict and determine the identified medical device 108A.

In block 506, the software application tool 112 determines whether the identified medical device 108 is an acceptable identification of the medical device 108 through, for example, instructions to make such a determination executed by the processor 304. As described above, the identification algorithm 312A may use one or more prediction confidence probabilities indicative of a confidence level associated with identification of the identified medical device 108A such that the matched type of medical device 108 is assigned a confidence level as a prediction confidence probability that must be greater than or equal to the confidence threshold value prior to being set as the identified medical device 108A.

As an additional or alternative non-limiting example, a user is presented with an option on the GUI 114 on the display screen 104 of the smart mobile device 102 of whether to accept the identified medical device 108A as acceptable or not. In at least one embodiment, the processor 304 is configured to execute one or more instructions to present the user with the option and receive a selection of the user whether to accept or reject the identification of the identified medical device 108A. In response to user rejection of the option to accept the identified medical device 108A, the software application tool 112 may be configured to capture another image 111 of the medical device 108 through use of the camera 106 to repeat the steps in blocks 502 and 504 until the user accepts the option to accept the identified medical device 108A. Alternatively, the software application tool 112 may be configured to repeat the steps in blocks 502 and 504 and present the user with an option to accept another identified medical device 108A until the user accepts the option. The software application tool 112 may further be configured to process the misclassified image 111 in an image database through, for example, use of the processor 304 to execute instruction steps as described herein to retrain a convolutional neural network such that the convolutional neural network is more likely to correctly identify the medical device 108 in a future application of the identification algorithm 312A. In at least one embodiment, in response to user rejection of the option to accept the identified medical device 108A, the software application tool 112 may be configured to display a warning that the medical device 108 in the image 111 is an unrecognized medical device type.

In response to acceptance by the user of the option to accept the identified medical device 108A, the process 505 proceeds to block 508. In block 508, one or more requirements of the identified medical device 108A are retrieved, including setup content. For example, the software application tool 112 on the smart mobile device 102 is automatically configured to retrieve data associated with one or more requirements of the identified medical device as retrieved data including at least setup content through, for example, one or more instructions executed by the processor 304. In at least one embodiment, the retrieved data may include country specific settings such as date and time display, metric units, and the like and update the software application tool 112 and/or identified medical device 108A with such settings. Further, menu options may be created and/or populated in the software application tool 112 associated with the identified medical device 108A and may include a list of compatible test strips, usage of test strips, pairing instructions such as whether manual or automatic, and the like. As described above, the software application tool 112 includes a GUI 114 on the display screen 104 of the smart mobile device 102. At least a portion of the retrieved data may be displayed to the user on the GUI 114 on the display screen 104 of the smart mobile device 102. The portion of the retrieved data may be displayed during setup of the software application tool 112 based on the identified medical device 108A and/or during use of the software application tool 112 to monitor the identified medical device 108A after pairing through, for example, one or more instructions executed by the processor 304.

For example, in block 510, retrieved data such as the setup content is utilized to pair the identified medical device 108A with the smart mobile device 102. The software application tool 112, for example, is paired with the identified medical device 108A through, for example, one or more instructions executed by the processor 304 and based on the setup content such that the smart mobile device 102 is communicatively coupled to the identified medical device 108A. In block 512, activity of the paired identified medical device 108A is monitored with the smart mobile device 102. As a non-limiting example, the software application tool 112 of the smart mobile device 102 is configured to monitor as a monitored activity the identified medical device 108A through, for example, one or more instructions executed by the processor 304. The monitored activity may include an administration of a prescribed treatment regime for the user through use of the identified medical device to administer the prescribed treatment regime.

In embodiments, the software application tool 112 may be configured to provide an alert on the GUI 114 and to the user of a failure in the administration of the prescribed treatment regime based on the monitored activity of the identified medical device by the software application tool 112. As a non-limiting example, the alert may be an audio, visual, and/or tactile alert provided to the user through the smart mobile device 102 upon detection of the failure in the administration of the prescribed treatment regime.

In medical device data manager configuration systems described herein, a software application tool 112 communicatively coupled to a smart mobile device 102 is configured to apply an identification algorithm 312A such as an image recognition algorithm through an identification tool component 312 to an image 111 captured by the smart mobile device 102. The software application tool 112 is thus able to automatically identify an identified medical device 108A through use of the identification algorithm 312A and a database 314 such as, for example, an image database on the cloud 323 or other database storage location. Such automatic identification streamlines a process to identify the medical device 108 as an identified medical device 108 to pair with the smart mobile device 102 by not requiring user selection, for example, of the medical device 108 from a listing of options, for example.

Such an automated data configuration system streamlines and more accurately and effectively adapts digital or data management solutions from a data manager such as the software application tool 112 to the identified medical device 108A on demand while minimizing dependencies on user involvement and know-how. Based on acceptance by the software application tool 112 through either an acceptable confidence value of the identification as described herein for automated acceptance or through user input of an acceptance of the identification of the presented identified medical device 108A, the software application tool 112 is configured to automatically retrieve data associated with the identified medical device 108A and to pair the identified medical device 108A with the smart mobile device 102. The user may then utilize the smart mobile device 102 to monitor activity of the identified medical device 108A such as use of the identified medical device 108A to administer a prescribed treatment regime to the user and user adherence to the prescribed treatment regime through use of the identified medical device 108A.

Item 1. A medical device data manager configuration system including a medical device, a smart mobile device including a camera, a processor, a memory communicatively coupled to the processor, and machine readable instructions stored in the memory that cause the medical device data manager configuration system to perform at least the following when executed by the processor: machine readable instructions stored in the memory that cause the medical device data manager configuration system to perform at least the following when executed by the processor; apply an identification algorithm to the image of the medical device; identify the medical device as an identified medical device based on the image of the medical device and the identification algorithm; and automatically configure a software application tool on the smart mobile device to retrieve data associated with one or more requirements of the identified medical device.

Item 2. The medical device data manager configuration system of item 1, wherein the machine readable instructions further comprise instructions to display the one or more requirements of the identified medical device on a graphical user interface (GUI) of the smart mobile device.

Item 3. The medical device data manager configuration system of items 1 or 2, wherein the one or more requirements of the identified medical device comprise content specific to the specific to the identified medical device, the content comprises at least one of onboarding content, communication management instructions, educational materials, regulatory labeling content, and one or more menu options.

Item 4. The medical device data manager configuration system of item 3, wherein the education materials comprise educational content associated with the identified medical device providing during a setup associated with the identified medical device.

Item 5. The medical device data manager configuration system of item 4, wherein the educational content comprises at least one of information about a compatible test strip, information about use of the compatible test strip with the identified medical device, and information about related calibration testing procedures.

Item 6. The medical device data manager configuration system of any of items 1 to 5, wherein the machine readable instructions further comprise instructions to pair the smart mobile device and the identified medical device.

Item 7. The medical device data manager configuration system of any of items 1 to 6, wherein the machine readable instructions further comprise instructions to automatically provide device specific pairing instructional information to a user regarding pairing prior to pairing the smart mobile device and the identified medical device.

Item 8. The medical device data manager configuration system of any of items 1 to 7, wherein the machine readable instructions further comprise instructions to at least one of automatically perform firmware version checks and install firmware updates associated with the identified medical device.

Item 9. The medical device data manager configuration system of any of items 1 to 8, wherein the identification algorithm comprises at least one of reading of a QR code and a serial number of the medical device.

Item 10. The medical device data manager configuration system of any of items 1 to 9, wherein the identification algorithm comprises an image recognition algorithm.

Item 11. The medical device data manager configuration system of item 10, wherein the image recognition algorithm is configured to utilize a trained convolutional neural network, the trained convolutional neural network configured to identify objects within an image to a high-level of accuracy.

Item 12. The medical device data manager configuration system of item 11, wherein the trained convolutional neural network and associated computations are stored in the smart mobile device and an image database is stored in a cloud networking environment, the trained convolutional neural network configured to be pre-trained on a subset of the image database.

Item 13. The medical device data manager configuration system of any of items 1 to 12, wherein the smart mobile device is configured to serve as a conduit to transfer the image to a cloud server of a cloud networking environment, and the cloud server is configured to store an image database and a convolutional network that are configured to interact with the identification algorithm to identify the medical device based on the image.

Item 14. The medical device data manager configuration system of item 13, wherein one or more identification calculations associated with the identification algorithm are conducted in the cloud networking environment, and class information associated with the identified medical device is transmitted to the smart mobile device from the cloud networking environment.

Item 15. The medical device data manager configuration system of any of items 1 to 14, wherein the software application tool is configured to display a reference frame on a display screen of the smart mobile device, the reference frame configured to identify an area to position the medical device within prior to image capture by the camera of the smart mobile device.

Item 16. A method of operating a medical device data manager configuration system, including capturing an image of a medical device through a camera on a smart mobile device; applying an identification algorithm to the image of the medical device; identifying the medical device as an identified medical device based on the image of the medical device and the identification algorithm; automatically configuring a software application tool on the smart mobile device to retrieve data associated with one or more requirements of the identified medical device as retrieved data, wherein the software application tool comprises a GUI on a display screen of the smart mobile device; pairing the software application tool with the identified medical device based on the retrieved data such that the smart mobile device is communicatively coupled to the identified medical device; monitoring, as a monitored activity of the identified medical device by the software application tool, an administration of a prescribed treatment regime for the user through use of the identified medical device to administer the prescribed treatment regime; and providing an alert on the GUI and to the user of a failure in the administration of the prescribed treatment regime based on the monitored activity of the identified medical device by the software application tool.

Item 17. The method of item 16, further including presenting an option to the user to accept the identified medical device, and automatically configuring a software application tool on the smart mobile device to retrieve the retrieved data in response to acceptance by the user of the option to accept of the identified medical device.

Item 18. The method of any of items 16 to 17, further including displaying to a user at least a portion of the retrieved data on the GUI on the display screen of the smart mobile device to inform the user of one or more requirements of the identified medical device.

Item 19. A method of operating a medical device data manager configuration system, including capturing an image of a medical device through a camera on a smart mobile device; applying an identification algorithm to the image of the medical device; identifying the medical device as an identified medical device based on the image of the medical device and the identification algorithm; presenting an option to the user to accept the identified medical device; in response to acceptance by the user of the option to accept of the identified medical device, automatically configuring a software application tool on the smart mobile device to retrieve data associated with one or more requirements of the identified medical device as retrieved data including at least setup content; pairing the software application tool with the identified medical device based on the setup content such that the smart mobile device is communicatively coupled to the identified medical device; and monitoring as a monitored activity the identified medical device by the software application tool of the smart mobile device.

Item 20. The method of item 19, wherein the monitored activity comprises an administration of a prescribed treatment regime for the user through use of the identified medical device.

Item 21. The method of any of items 16-20, including the medical device data manager configuration system of any of items 1-15.

Item 22. A processor for a medical device data manager configuration system including a medical device and a smart mobile device including a camera, the processor configured to execute machine readable instructions stored in a memory communicatively coupled to the processor to perform at least the following; use the camera of the smart mobile device to capture an image of the medical device; apply an identification algorithm to the image of the medical device; identify the medical device as an identified medical device based on the image of the medical device and the identification algorithm; and automatically configure a software application tool on the smart mobile device to retrieve data associated with one or more requirements of the identified medical device.

Item 23. The processor of item 22, wherein the smart mobile device is communicatively coupled to the processor.

Item 24. The processor of item 23, wherein the medical device data manager configuration system is communicatively coupled to the processor.

Item 25. The processor of any of items 21-24, including the medical device data manager configuration system of any of items 1-15.

Item 26. The method of any of items 16-20, including the processor of any of items 21-25.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A medical device data manager configuration system comprising:
   a medical device configured to administer a prescribed treatment regime for a user;
   a smart mobile device including a camera;
   a processor;
   a memory communicatively coupled to the processor; and
   machine readable instructions stored in the memory that cause the medical device data manager configuration system to perform at least the following when executed by the processor:
   use the camera of the smart mobile device to capture an image of the medical device;
   apply an identification algorithm to the image of the medical device;
   identify the medical device as an identified medical device based on the image of the medical device and the identification algorithm;
   automatically configure a software application tool downloaded on the smart mobile device to retrieve data associated with one or more operational requirements of the identified medical device to update configuration of the software application tool based on the retrieved data such that the software application tool is configured to monitor activity of the identified medical device; and
   pair the smart mobile device and the identified medical device to monitor activity of the identified medical device by the software application tool.

2. The medical device data manager configuration system of claim 1, wherein the machine readable instructions further comprise instructions to display the one or more requirements of the identified medical device on a graphical user interface (GUI) of the smart mobile device.

3. The medical device data manager configuration system of claim 1, wherein the one or more requirements of the identified medical device comprise content specific to the specific to the identified medical device, the content comprises at least one of onboarding content, communication management instructions, educational materials, regulatory labeling content, and one or more menu options.

4. The medical device data manager configuration system of claim 3, wherein the education materials comprise educational content associated with the identified medical device providing during a setup associated with the identified medical device.

5. The medical device data manager configuration system of claim 4, wherein the educational content comprises at least one of information about a compatible test strip, information about use of the compatible test strip with the identified medical device, and information about related calibration testing procedures.

6. The medical device data manager configuration system of claim 1, wherein the machine readable instructions further comprise instructions to automatically provide device specific pairing instructional information to a user regarding pairing prior to pairing the smart mobile device and the identified medical device.

7. The medical device data manager configuration system of claim 1, wherein the machine readable instructions further comprise instructions to at least one of automatically perform firmware version checks and install firmware updates associated with the identified medical device.

8. The medical device data manager configuration system of claim 1, wherein the identification algorithm comprises at least one of reading of a QR code and a serial number of the medical device.

9. The medical device data manager configuration system of claim 1, wherein the identification algorithm comprises an image recognition algorithm.

10. The medical device data manager configuration system of claim 9, wherein the image recognition algorithm is configured to utilize a trained convolutional neural network, the trained convolutional neural network configured to identify objects within an image to a high-level of accuracy.

11. The medical device data manager configuration system of claim 10, wherein the trained convolutional neural network and associated computations are stored in the smart mobile device and an image database is stored in a cloud networking environment, the trained convolutional neural network configured to be pre-trained on a subset of the image database.

12. The medical device data manager configuration system of claim 1, wherein the smart mobile device is configured to serve as a conduit to transfer the image to a cloud server of a cloud networking environment, and the cloud server is configured to store an image database and a convolutional network that are configured to interact with the identification algorithm to identify the medical device based on the image.

13. The medical device data manager configuration system of claim 12, wherein one or more identification calculations associated with the identification algorithm are conducted in the cloud networking environment, and class information associated with the identified medical device is transmitted to the smart mobile device from the cloud networking environment.

14. The medical device data manager configuration system of claim 1, wherein the software application tool is configured to display a reference frame on a display screen of the smart mobile device, the reference frame configured to identify an area to position the medical device within prior to image capture by the camera of the smart mobile device.

15. A method of operating a medical device data manager configuration system, comprising:
- capturing an image of a medical device through a camera on a smart mobile device;
- applying an identification algorithm to the image of the medical device, the medical device configured to administer a prescribed treatment regime;
- identifying the medical device as an identified medical device based on the image of the medical device and the identification algorithm;
- automatically configuring a software application tool downloaded on the smart mobile device to retrieve data associated with one or more operational requirements of the identified medical device as retrieved data to update configuration of the software application tool based on the retrieved data, wherein the software application tool comprises a GUI on a display screen of the smart mobile device;
- pairing the software application tool with the identified medical device based on the retrieved data such that the smart mobile device is communicatively coupled to the identified medical device;
- monitoring, as a monitored activity of the identified medical device by the software application tool, an administration of the prescribed treatment regime for a user through use of the identified medical device to administer the prescribed treatment regime; and
- providing an alert on the GUI and to the user of a failure in the administration of the prescribed treatment regime based on the monitored activity of the identified medical device by the software application tool.

16. The method of claim 15, further comprising presenting an option to the user to accept the identified medical device, and automatically configuring a software application tool on the smart mobile device to retrieve the retrieved data in response to acceptance by the user of the option to accept of the identified medical device.

17. The method of claim 15, further comprising displaying to the user at least a portion of the retrieved data on the GUI on the display screen of the smart mobile device to inform the user of one or more requirements of the identified medical device.

18. A method of operating a medical device data manager configuration system, comprising:
- capturing an image of a medical device through a camera on a smart mobile device, the medical device configured to administer a prescribed treatment regime for a user;
- applying an identification algorithm to the image of the medical device;
- identifying the medical device as an identified medical device based on the image of the medical device and the identification algorithm;
- presenting an option to the user to accept the identified medical device;
- in response to acceptance by the user of the option to accept of the identified medical device, automatically configuring a software application tool downloaded on the smart mobile device to retrieve data associated with one or more operational requirements of the identified medical device as retrieved data including at least setup content to update configuration of the software application tool based on the retrieved data;
- pairing the software application tool with the identified medical device based on the setup content such that the smart mobile device is communicatively coupled to the identified medical device; and
- monitoring as a monitored activity the identified medical device by the software application tool of the smart mobile device.

19. The method of claim 18, wherein the monitored activity comprises an administration of the prescribed treatment regime for the user through use of the identified medical device.

* * * * *